(12) United States Patent
Miettinen

(10) Patent No.: US 9,173,578 B2
(45) Date of Patent: Nov. 3, 2015

(54) HEART PULSE DETECTION

(75) Inventor: Jari Miettinen, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 331 days.

(21) Appl. No.: 13/070,925

(22) Filed: Mar. 24, 2011

(65) Prior Publication Data
US 2011/0245697 A1    Oct. 6, 2011

(30) Foreign Application Priority Data

Mar. 31, 2010  (FI) ...................................... 20105335

(51) Int. Cl.
*A61B 5/024*  (2006.01)
*A61B 5/00*  (2006.01)

(52) U.S. Cl.
CPC ......... *A61B 5/02416* (2013.01); *A61B 5/02438* (2013.01); *A61B 5/681* (2013.01); *A61B 5/6814* (2013.01); *A61B 5/6828* (2013.01); *A61B 5/7214* (2013.01); *A61B 5/6824* (2013.01)

(58) Field of Classification Search
CPC ............... A61B 5/02416; A61B 5/681; A61B 5/02438; A61B 5/6814; A61B 5/6828; A61B 5/7214; A61B 5/6824
USPC ......... 600/500, 507, 504, 503, 502, 501, 481, 600/483
See application file for complete search history.

(56) References Cited

U.S. PATENT DOCUMENTS

| | | | |
|---|---|---|---|
| 4,164,937 A | 8/1979 | Spencer | |
| 6,413,223 B1 * | 7/2002 | Yang et al. | 600/485 |
| 2002/0045806 A1 * | 4/2002 | Baker et al. | 600/309 |
| 2002/0177782 A1 * | 11/2002 | Penner | 600/485 |
| 2003/0065269 A1 * | 4/2003 | Vetter et al. | 600/503 |
| 2005/0228253 A1 * | 10/2005 | Debreczeny | 600/407 |
| 2006/0122520 A1 | 6/2006 | Banet et al. | |
| 2006/0281983 A1 * | 12/2006 | Al-Ali et al. | 600/323 |
| 2007/0055163 A1 * | 3/2007 | Asada et al. | 600/485 |
| 2007/0276261 A1 | 11/2007 | Banet et al. | |
| 2008/0039731 A1 * | 2/2008 | McCombie et al. | 600/485 |
| 2009/0054751 A1 | 2/2009 | Babashan et al. | |

(Continued)

FOREIGN PATENT DOCUMENTS

| | | |
|---|---|---|
| EP | 1297784 A1 | 4/2003 |
| WO | WO9817172 A2 | 4/1998 |

OTHER PUBLICATIONS

Verkruysse et al., Remote plethysmographic imaging using ambient light, Optics Express, 16(26), Dec. 2008, pp. 21434-21445.*
Aidan Doyle, Extended European Search Report for European application corresponding to U.S. Appl. No. 13/070,925, Munich, pp. 1-7 (Jul. 8, 2011).

(Continued)

*Primary Examiner* — Michael Kahelin
*Assistant Examiner* — Tho Tran
(74) *Attorney, Agent, or Firm* — Hoffmann & Baron, LLP

(57) ABSTRACT

There is provided an apparatus for determining a heart pulse of a person, the apparatus comprising at least two detectors configured to detect a blood pulse optically from the blood circulation of the person and to be placed optically on the skin of the person such that the detection of the blood pulse by each of the at least two detectors is expected to take place in a known order, a processor configured to determine that the detection of the blood pulse is correct when the detection of the blood pulse by each of the at least two detectors takes place in the known order, and to determine the heart pulse of the person on the basis of the detected pulses that are determined as correct.

14 Claims, 4 Drawing Sheets

(56) References Cited

U.S. PATENT DOCUMENTS

2009/0171172 A1    7/2009   Bordon et al.
2013/0006130 A1*   1/2013   Olde et al. .................... 600/504

OTHER PUBLICATIONS

Tuomo Reiniaho, Finnish Search Report for Finnish application corresponding to U.S. Appl. No. 13/070,925, Finland, pp. 1-2 (2011).

* cited by examiner

HEART PULSE DETECTION

CROSS-REFERENCE TO RELATED APPLICATION

This application claims priority based on Finnish Application No. 20105335, filed Mar. 31, 2010, which is incorporated herein by reference.

BACKGROUND

1. Field

The invention relates generally to heart pulse detection.

2. Description of the Related Art

It is desirable for a person exercising to be aware of his/her heart rate. It is common to measure the heart pulses with a strap attached to the user's chest, wherein electrodes in the strap detect an electrocardiogram (ECG) signal of the user. The heart rate is calculated from the heart pulses. The ECG signal is an electromagnetic signal generated by the heart muscle of a person and detectable on the person's skin. Further, it is known to measure the heartbeat signal from body parts other than the chest, such as a tip of a finger. However, drawbacks of the current detection techniques include the complexity of wearing an additional structure and/or unreliability of the results obtained.

SUMMARY

The present invention seeks to provide an improved solution for heart pulse determination.

According to an aspect of the invention, there is provided an apparatus.

BRIEF DESCRIPTION OF THE DRAWINGS

In the following, the invention will be described in greater detail with reference to embodiments and the accompanying drawings, in which.

DETAILED DESCRIPTION

The following embodiments are exemplary. Although the specification may refer to "an", "one", or "some" embodiment(s) in several locations of the text, this does not necessarily mean that each reference is made to the same embodiment(s), or that a particular feature only applies to a single embodiment.

Figure 1:
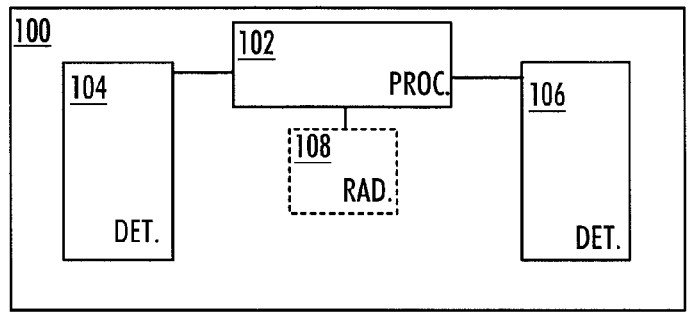
FIG. 1 presents an apparatus according to an embodiment.
Figure 2:
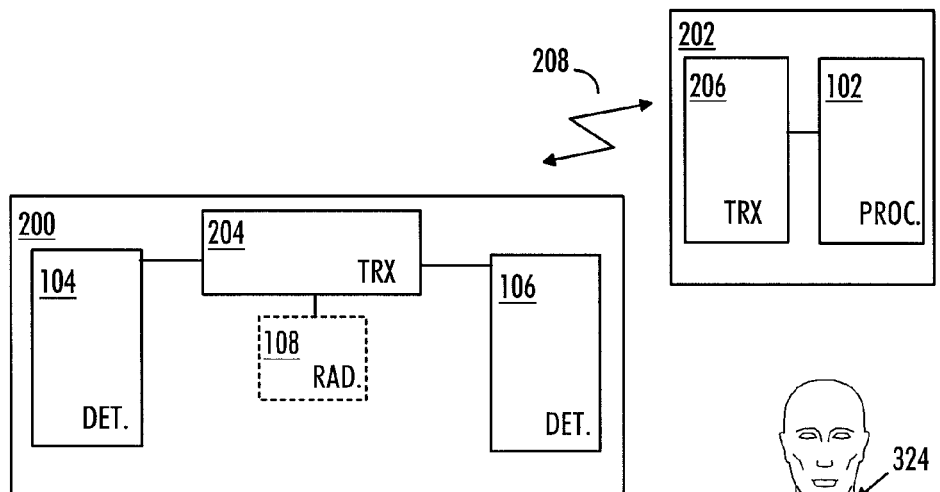
FIG. 2 shows an apparatus according to an embodiment.

A very general architecture of apparatuses according to two embodiments is shown in FIGS. 1 and 2. The figures show only the elements and functional entities required for understanding the apparatuses according to the embodiments. Other components have been omitted for reasons of simplicity. The implementation of the elements and functional entities may vary from that shown in FIGS. 1 and 2. The connections shown in FIGS. 1 and 2 are logical connections, and the actual physical connections may be different. The connections can be direct or indirect and there can merely be a functional relationship between components. It is apparent to a person skilled in the art that the apparatus for determining heart pulses of a person may also comprise other functions and structures.

FIG. 1 shows an apparatus 100 for determining heart pulses of a person. The apparatus 100 comprises at least two detectors 104 and 106 for detecting a blood pulse optically from the blood circulation of the person. The detection of the blood pulse is based on a non-invasive optical measurement through the human skin. The detection may also be understood as measurement, observation, monitoring, etc. The at least two detectors 104 and 106 may be optical detectors that are sensitive to optical radiation. The at least two detectors 104 and 106 may thus be photodiodes, photoconductive cells, or any other components sensitive to optical radiation.

Heart pulses may be used for characterizing a user's cardiovascular activity. Heart pulses may be applied for calculating a heart rate, i.e. the frequency of heart beats, heart beat intervals, and/or heart rate variability.

It is beneficial to use at least two detectors 104 and 106 because the optical heart pulse detection is sensitive to motion artifacts. This causes measurement errors which arise from the fact that the optical transmission coefficient may not be stable due to motion artifacts. On one hand, a change in the optical transmission coefficient may be caused by the motion between the detector optics and the skin, and on the other hand, if an optical radiation source 108 is used, by motion between the radiation source 108 and the skin. Motion artifacts may be arbitrary or regular. The detector 104 and/or 106 may move away from the blood circulation vessel from which the blood pulse is supposed to be detected, and the distance between the skin and the detector 104 and/or 106 may vary, for example. The arbitrary motion artifacts arise from instantaneous unexpected body movements, while regular artifacts typically arise from the human rhythmic motion, such as walking or running. The motion artifacts may fall to the same frequency range as the heart pulses, and the two components cannot be separated from each other. This results in an erroneous heart pulse and/or heart activity assessment. According to an embodiment, the motion artifacts are eliminated from being taken into account in the heart pulse determination by measuring the blood pulses at two measurement points along the blood circulation system, wherein the pulse delay and order of the pulses are known between the measurement locations. By having at least two detectors 104 and 106 present in the apparatus 100, the reliability of the detection is improved significantly.

Figure 3:
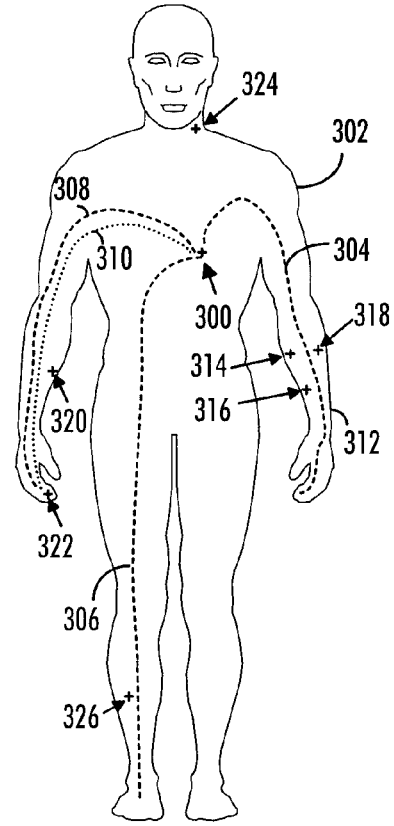
FIG. 3 illustrates a person's blood circulation.

Let us discuss the human blood circulation in more detail with reference to FIG. 3. As the heart muscle 300 of a person 302 contracts, oxygenated blood is pumped to the cardiovascular system, which results in a blood pressure alteration in the blood circulation. The oxygenated blood is pumped through the arterial circulation system 304 to 308 to human cells. For the sake of simplicity, only few arterials are shown in FIG. 3. Naturally, human body comprises more arterials than those shown. The blood is deoxygenated in the human cells and returned back to the heart via a venous circulatory system 310. Again, for simplicity reasons only one vein 308 is shown. As the blood circulates in the arterials 304 to 308 and in the veins 308, the blood pressure pulses can be observed from both of them. Moreover, the human blood circulation is a closed system, meaning that exactly the same amount of blood is pumped from the heart as is received by the heart. This enables the same modulation of blood pulses to be observed from the veins 308 as from the arteries 304 to 308. Further, blood travels also in a person's microcirculation system (also known as a microvascular blood flow or a microvascular system) and, therefore, the blood pressure pulse can be detected from the skin's microcirculation, as well.

According to an embodiment, the at least two detectors 104 and 106 may be placed optically on the skin of the person 302. The detectors 104 and 106 may be placed such that the detection of the blood pulse by each of the at least two detectors 104 and 106 is expected to take place in a known order. Suitable places for detection of the blood pulse are places 314 and 316 marked with plusses in FIG. 3, for example. The places 314 and 316 may be on the human skin along one of the following: the arterial blood flow, the venous blood flow, or the microcirculation system, of the person 302. Thus, the at least two detectors 104 and 106 may detect the blood pulse from at least one corresponding blood transport means.

The word "optically" means that there may be some element(s) between the skin of the person 302 and the detectors 104 and 106 as long as the element is optically transparent or at least allows optical radiation to penetrate. When the optical radiation can penetrate the element(s), the detection is possible. Therefore, a glass or a plastic shield for covering the surface of the detector 104 and 106 is suitable, for example. According to an embodiment, there is a shield between the skin and the detector and/or between the skin and the optical radiation source. The shield may have a refractive index which is substantially the same as the skin's refractive index is. This is beneficial so that the light received by the detector 104 and 106 and/or the optical radiation source does not become distorted due to the shield. This also aids in avoiding undesired reflections from the shield. Accordingly, the detector 104 and 106 do not have to be directly on the skin of the person 302 but an indirect optical connection is sufficient.

When the two detectors 104 and 106 are along an artery, the known order for detections of the blood pulse is such that the detector at a location 314 detects the blood pressure pulse first and the detector at a location 316 detects the same blood pressure pulse second. This is due to the fact that blood in the arteries flow away from the heart 300. On the other hand, if the locations 314 and 316 were along a vein of the person 302, the known order for detections of the blood pulse would be vice versa, that is, the detector at the location 316 detects the blood pressure pulse first and the detector at the location 314 detects the same blood pressure pulse second. Detection from skin's microcirculation follows the same order as the detection from the artery.

However, the places for the at least two detectors 104 and 106 may not have to be at locations 314 and 316. In an embodiment, one of the at least two detectors 104 and 106 is placed at a location 316 on the wrist 312 of the person 302 whereas the other of the at least two detectors 104 and 106 is placed on the other hand at a location 320 or 322, for example. This is possible because in this case also, the distance from the origin of the blood pulse, i.e., the heart, 300, is different for the two locations 316 and 320/322, and therefore the time instant for the detection of the blood pulse by the two detectors is different. Therefore, one detection takes place before another detection. FIG. 3 shows also other possible detection places with reference numerals 324 and 326. However, it should be noted that the detection of the blood pulse by a detector may take place at any location of the human body as long as the point of detection is along one of an artery, a vein, and a microcirculation system. Naturally, certain places are more attractive for detecting the blood pulse but in general any point on the human skin suffices for the detection.

As the blood pulse travels in the human body at a known velocity or at least at a velocity that can be measured, the detection of the blood pulse by each of the at least two detectors 104 and 106 is expected to take place in a known time difference between each of the detections. For example, if the blood flows one centimeter during one millisecond, the distance of three centimeters between the two detectors 104 and 106 in relation to the heart 300 equals a three millisecond time difference between the detections of the blood pulse by the detectors 104 and 106. It should be noted that the distance between the two or more detectors 104 and 106 is measured in relation to the heart 300 as the origin of the blood pressure pulse. Having one detector 104 in the leg at a location 326 with a distance $d_1$ from the heart 300 and another detector 106 on the wrist 312 at a location 314 with a distance $d_2$ from the heart 300 causes a distance d between the detectors 104 and 106 in relation to the heart 300 to be $abs(d_1-d_2)$, that is, the absolute value of the difference between distances $d_1$ and $d_2$.

The apparatus 100, 202 for determining a heart pulse of the person 302 may further comprise a processor 102. The processor 102 may be implemented with a separate digital signal processor provided with suitable software embedded on a computer readable medium, or with a separate logic circuit, such as an application specific integrated circuit (ASIC). The processor 102 may comprise an interface, such as a computer port, for providing communication capabilities. The processor 102 may be, for example, a dual-core processor or a multiple-core processor. The apparatus may also comprise a memory connected to the processor 102. However, memory may also be integrated to the processor 102 and, thus, no separate memory may be required.

According to an embodiment, the processor 102 may determine that a blood pulse has been detected when the detections by the at least two detectors 104 and 106 take place in the known order. In this case, it can be said that the detection of the blood pulse is correct, valid or successful. If the detection by the at least two detectors 104 and 106 does not take place in the known order, the detection may be determined as false or erroneous. Only the successful detections may be taken into account. That is, the false or erroneous detections may be disregarded from the heart pulse determination.

The processor 102 may determine the heart pulse of the person on the basis of the detected blood pulse. Heart pulses may be used for characterizing a user's cardiovascular activity. The processor 102 may apply the knowledge of the detected heart pulses in determining various parameters including a heart rate, i.e. the frequency of heart beats, heart beat intervals, and/or heart rate variability, etc. The determined information may be displayed to a user wearing the apparatus so that he or she can apply the information when exercising or when planning an exercise.

Further, the processor 102 may also consider whether or not the time difference between the detections is as expected. That is, the processor 102 may determine that a blood pulse has been detected when the detections by the at least two detectors 104, 106 are separated by known time differences. In the case of two detectors 104 and 106, there is only one known time difference. However, when there are three or more detectors, there may be two or more time differences which can be the same or different. That is, there may be one time difference $t_{1-2}$ between the first and the second detector and another time difference $t_{2-3}$ between the second and the third detector. The time differences $t_{1-2}$ and $t_{2-3}$ may or may not be the same. When the detections by the at least two detectors 104, 106 are separated by known time differences, it can be said that the detection of the blood pulse is correct, valid or successful.

Figure 4:
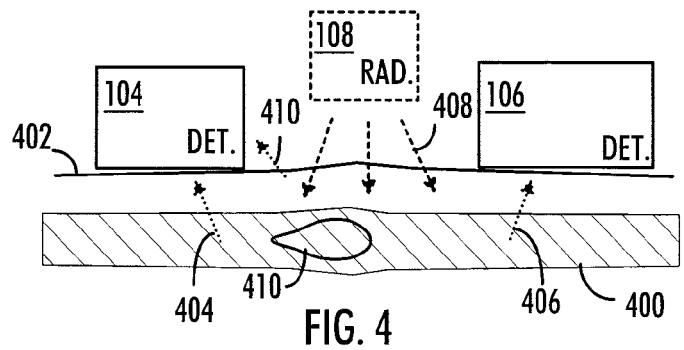
FIG. 4 shows how detection of a blood pulse is performed according to an embodiment.

Let us next discuss how the optical detection of the blood pulse from the blood circulation 400 of the person 302 may take place with reference to FIG. 4, wherein the blood circulation 400 of the person 302 comprises the arterial blood flow, the venous blood flow, and the microcirculation blood flow. FIG. 4 illustrates a point on human skin 402 that is selected as the point for detection of the blood pulse 410 from the blood circulation part 400.

In the blood pulse measurement, the human tissue is subjected to optical radiation 408, as shown with dashed lines in FIG. 4, which radiation penetrates through the human skin 402. One portion of the radiation is scattered in the tissue, while another portion is absorbed. The absorbed portion of the radiation is modulated by the chemical absorbers of blood in the circulation 400 at the frequency of heart pulses, while the scattering portion is independent of the blood flow. The optical measurement aims at measuring a reflected component 404 and 406 as shown with dotted arrows in FIG. 4. The reflected optical radiation 404 and 406 is modulated at the frequency of absorption, i.e. at the frequency of the heart activity.

According to an embodiment, the at least two detectors 104 and 106 may detect a variation in an optical radiation 404 and 406 reflected from the human tissue in order to detect a blood pulse 410 from the blood circulation part 400 optically. This means that the two optical sensors 104 and 106 measure the variation of the power of the reflected optical radiation 404 and 406. The variation is due to absorption or scattering when the amount of blood in the measurement volume, i.e. in the circulation part 400, varies. For instance, when there is a blood pulse 410 in the blood circulation part 400, the blood absorbs/scatters more optical radiation 408 than when there is no blood pulse 410 in the circulation part 400.

As can be seen in FIG. 4, the detectors 104 and 106 and the optical radiation source 108 are on the same side of the human tissue, instead of being on opposite sides (for example, on opposite sides of a finger). Therefore, the detectors 104 and 106 utilize the reflected radiation 404 and 406 instead of the radiation possibly penetrating the tissue. This enables detection from body parts having such a thickness that the optical radiation cannot protrude the tissue. Therefore, freedom in choosing the detection location is provided by this embodiment.

As shown in FIGS. 1, 2, and 4, the apparatus 100, 200 may further comprise at least one optical radiation source 108 configured to provide optical radiation 408 such that the at least two detectors 104 and 106 are able to detect the optical radiation 404 and 406 reflected from the human tissue. When there are two detectors located relatively close to each other, a suitable location for providing the optical radiation 408 in relation to the two detectors 104 and 106 may be in the middle of the two detectors 104 and 106, for example. This way both of the detectors may detect the reflected optical radiation because the location where the optical radiation is provided is not too far. The optimum location for providing the optical radiation 408 may be searched for by empirically trying different places for providing the optical radiation 408 in terms of the at least two detectors 104 and 106 being able to detect the reflected radiation. If the at least two detectors 104 and 106 are located far from each other, there may be at least two different optical radiation sources 108, one for each detector 104 and 106. The optical radiation source 108 may be a light emitting diode (LED) or an organic LED (OLED), for example. The optical radiation 408 may be emitted directly from the radiation source 108 to the skin of the person, or the optical radiation may be conveyed to the illuminated point of the skin via an optical fiber cable, for example. There may be a plurality of adjacent optical radiation sources 108 to provide optical radiation towards the part of the blood circulation from which the detection of the blood pulse is performed.

The wavelength of the optical radiation 408 may be predetermined such that it allows the optical radiation to be absorbed in the blood in the most efficient way. According to an embodiment, the provided optical radiation 408 has a wavelength of one of the following: 660 nm and 940 nm. The wavelength of 660 nm is especially suitable for detecting oxygenous blood, i.e. the blood travelling in the arteries or in the skin's microcirculation. This is because optical radiation with such a wavelength absorbs more efficiently in the oxygenous blood than optical radiation having another wavelength. Therefore, when the at least two detectors 104 and 106 are determined to detect the blood pressure pulse from either arteries or the microcirculation, the radiation source 108 may be determined to provide optical radiation having a wavelength of 660 nm. On the other hand, if the at least two detectors 104 and 106 are determined to detect the blood pressure pulse from the venous blood flow, the radiation source 108 may be determined to provide optical radiation having a wavelength of 940 nm. This is because the wavelength of 940 nm is absorbed especially efficiently by non-oxygenous blood. The wavelength of 660 nm represents red light, whereas the wavelength of 940 nm represents infrared light. Furthermore, these types of wavelengths are especially useful because such light does not become significantly absorbed by any other fluids, tissues, bones, etc.

However, no existence of the optical radiation source 108 is compulsory, hence the dotted illustration of the component 108 in the figures. According to an embodiment, the apparatus further comprises a signal processing chain. The at least two detectors 104 and 106 may be connected to the signal processing chain. The signal processing chain may generate heart pulse information from signals obtained from the at least two detectors, wherein the signals represent detected blood pulses. The signal processing chain may comprise amplifier(s), filter(s), an analog-to-digital converter, and the processor 102. The signal processing chain may be configured to be sensitive enough to enable detection of the blood pulse optically when the reflected optical radiation 404 and 406 to be detected origins only from ambient optical radiation. This is possible when the detectors are designed to detect optical radiation with a low power. Thus, in this case there is no separate optical radiation source 408 except for the light coming from the surroundings of the person wearing the apparatus for detecting the blood pulse.

When an optical radiation source 108 is present, there is a further possibility to detect the blood pulse 410 from the part 400 of the blood circulation in addition to or instead of the one based on variation of the reflected optical radiation 404, 406. According to another embodiment, the detection of the blood pressure pulse 410 may be based on the blood pressure pulse 410 causing, at the point of the pulse 410, enlargement of the blood circulation part 400 and the surrounding skin 402 area every time a heart pulse passes through the part 400, as shown in FIG. 4. The detector 104/106 then detects the movement of the skin 402 by detecting the changes during the time between the transmittal of the light 408 from the optical radiation source 108 and reception of the reflected light 410 because the skin 402 reflects a portion of the transmitted light 408. The movement of the skin 402 takes place at the heart rate when no errors, such as motion artifacts, occur. One of the advantages of this type of detection, which is also called optical interferometry, in cardiovascular pulse detection, is that the velocity profile of the movement of the arterial wall caused by the pressure pulse can be measured accurately. This enables the pulse amplitude to be measured reliably, for example.

FIG. 2 shows an embodiment comprising a gauge unit 200 equipped with the at least two detectors 104 and 106, the at least one light source 108 (not mandatory) and a transmitter 204 configured to transmit the detection results to a main unit 202 equipped with another transceiver 206 and the processor 102. The TRXs 204 and 206 may transmit information between each other via a wired connection or wirelessly. The TRXs 204 and 206 may transmit information regarding the detections of the blood pulse wirelessly 208 during operation. The information may be transmitted in a radio frequency signal 208. Further, for example, the radio frequency transmission 208 may utilize the Bluetooth® standard, or any other suitable standard/non-standard wireless communication methods utilizing electric and/or magnetic fields. An exemplary frequency for this type of transmission is 2.4 GHz, for instance. The units 200 and 202 may, thus, comprise antennas for accessing the radio interface. Alternatively, the transmission may be performed via magnetic pulses that are transmitted through coils in the units 200, 202. An exemplary frequency for this type of transmission is 5.5 kHz.

The gauge unit 200 may be worn by a person on his wrist, leg, forehead, etc. Thus, the gauge unit 200 may be located in the upper part of the arm, for example, thus resulting in a longer delay between the heart pulses and thus providing an improved capability to rule out erroneous pulse detections. The gauge unit 200 may be a strap-like structure which may be strapped around the user's arm, for example. The gauge unit 200 may be taken off when not performing exercise and put on when exercising. The main unit 202 may be worn by the person on his or her wrist as part of a wrist watch, hips, etc. It may also be carried along in a pocket, for example. In an embodiment, the main unit 202 is part of a wrist watch or a personal exercise computer unit, such as a wrist computer manufactured by Polar. Having a separate gauge unit 200 allows for the freedom to take the gauge unit 200 off while still keeping the main unit 202 still on. The embodiment also allows freedom in placing the gauge unit 200, because the user may not have to have a visual connection to the gauge unit 200. The main unit 202 may further be equipped with a display for displaying information to the person wearing the unit.

In another embodiment, as shown in FIG. 1, the processor 102 and the at least two electrodes 104 and 106 are in the same apparatus 100. The apparatus 100 may be a wrist unit, a wrist watch, or a personal exercise computer, such as a wrist computer manufactured by Polar, for example. These types of wrist devices typically comprise a main unit and at least one wrist band (typically two connectable wrist bands). According to an embodiment, the processor 102 is comprised in the main unit of a wrist device. This embodiment is shown in FIGS. 5A to 5D. However, even though the figures show the two detectors 104 and 106 as being on the same side of the wrist carrying the wrist device, this is not necessary. According to one embodiment, one detector, for example 104, is at the back side of the wrist while another detector 106 is on the palm side of the wrist. In this case, separate radiation sources may be present.

Figure 5A:
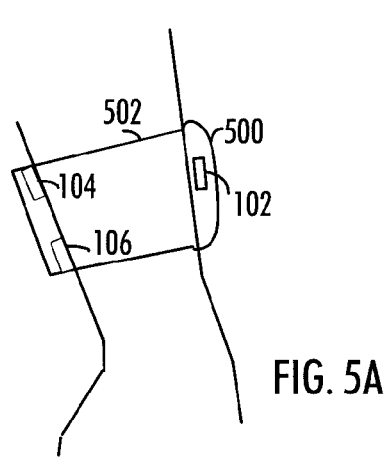
FIGS. 5A, 5B, 5C, and 5D illustrate wrist units according to different embodiments.

FIG. 5A shows a processor 102 in the main unit 500 of the wrist device. The main unit 500 may also comprise a display for displaying heart activity information, such as a heart rate, heart beat interval and/or heart rate variability, to the user. The at least two detectors are comprised in at least one wristband 502 of the wrist device. The at least two detectors 104 and 106 are advantageously placed on the palm side of the wrist so that they are able to detect the blood pulse travelling in an artery or in a vein of the palm side of the wrist. In this embodiment, there is no separate radiation source other than the ambient optical radiation. There may be a data connection link embodied in the wrist band 502 for connecting the at least two detectors 104 and 106 although not shown in FIG. 5A. Alternatively, there may be a wireless transmitter coupled to the at least two detectors 104 and 106, and a wireless receiver coupled to the processor 102 in order for them to exchange information related to the blood pulse detection.

Figure 5B:
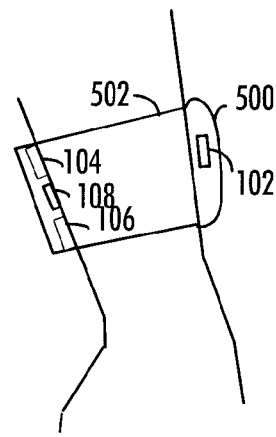

FIG. 5B is similar to FIG. 5A, except now there is a separate optical radiation source 108 present. There may be only one optical light source 108 providing illumination in such a way that each of the at least two detectors 104 and 106 may detect the reflected optical radiation. In this case, the optical radiation source 108 may be positioned between the two detectors 104 and 106. Alternatively, each of the at least two detectors 104 and 106 may be equipped with an optical radiation source of their own (although not shown in FIG. 5B).

The processor 102 may guide the optical radiation source 108 so that the optical radiation source 108 knows when to start providing radiation, for example. Alternatively, the optical radiation source 108 may be equipped with a sensor so that it knows when the optical radiation source 108 needs to be activated. This may happen, for example, when the optical radiation source 108 is brought into contact with the skin of the person. In this case the sensor may be a touch sensor.

Figure 5C:
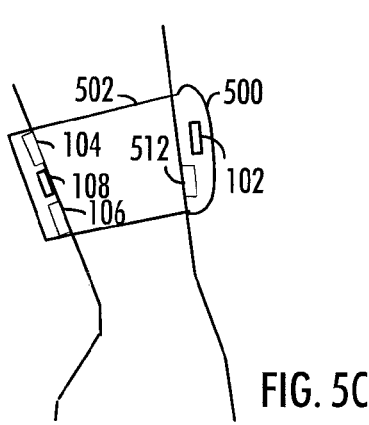
Figure 5D:
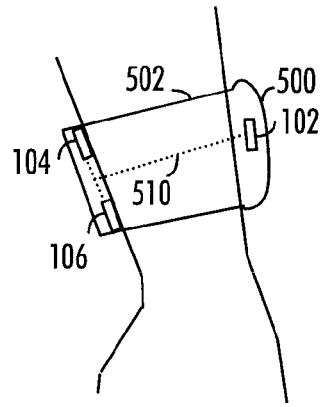

FIG. 5D shows an alternative to FIG. 5B in terms of optical radiation source. In this embodiment, the apparatus further comprises at least one optical radiation guide 510 embodied in the at least one wrist band 502. The optical radiation guide may be an optical fiber, for example. The optical radiation guide 510 may convey optical radiation from the optical radiation source to an area of the skin such that the at least two detectors 104 and 106 are able to detect the reflected optical radiation. That is, the optical radiation guide 510 may provide each of the detectors 104 and 106 with an illumination aperture of their own, or the optical radiation guide 510 may provide the detectors with one joint optical radiation aperture, for example, between the at least two detectors 104 and 106. In the case of more than two detectors aligned along the wrist, the optical radiation aperture may be located in the middle of the two farthermost detectors. This embodiment allows the wrist band 502 to be embodied with the optical radiation guide 510. Further, instead of having to place the optical radiation source 108 in the wrist band 502, the optical radiation source may be present in the main unit 500. The main unit 500 may be a more robust place to implement the optical radiation source than the wrist band 502.

The detection of the pulse may lead to obtaining knowledge of at least one of the following: the time instant, form and phase of the blood pulse. The time instant may determined by detecting the variation in the reflected optical radiation by the detectors. When the variation changes by a predetermined threshold, the processor may determine that a blood pulse travelled next to the detector which informed the processor about the variation in the reflected optical radiation. The processor may consequently time stamp the time instant as the time instant of the pulse. By obtaining the information from multiple detectors, the processor may determine whether or not the order of the detections and the time difference between the detections are valid, so that the detection can be determined as correct.

The use of two detectors 104 and 106 further allows the direction of the blood flow to be determined. In order to detect the blood pulse by each of the at least two detectors 104 and 106, the detectors 104 and 106 may be separated by, for example, one centimeter and the detection frequency is in the order of 1 kHz. This enables the detectors 14 and 106 to detect the same blood pulse travelling. The measurement of the direction of the blood movement may be based on a known propagation velocity of a blood pulse in the blood circulation system. Further, the direction can be assessed from the phase difference in the blood pulse observed at two locations.

In terms of blood circulation, a hand is a closed system. The arteries bring in just the same amount of blood as the veins take out. The blood in the artery is oxygenated whereas the blood in the veins is non-oxygenated, but carrying carbon dioxide. By applying appropriate wavelengths in the optical radiation, the two different types of blood can be distinguished. Further, the direction of movement of the distinguished blood may be extracted.

The form and phase of the pulse are determined by detecting the amount of variation observed in the reflected optical radiation. When there is a large drop in the amount of the reflected optical radiation observed at a certain time instant, then there most likely is a blood pulse present. By analyzing the amount of detected reflected radiation, the processor may obtain knowledge of the form and phase of the blood pulse. A large drop in the amount or power of the reflected optical radiation implies a blood pulse with a larger pulse form (higher amplitude of the pulse form) than a small drop in the amount or power of the reflected optical radiation. By detecting the variation in the optical radiation, the absolute value of the amplitude may not be known, but the form of pulse in relation to other detected pulse forms may be obtained.

Figure 6A:
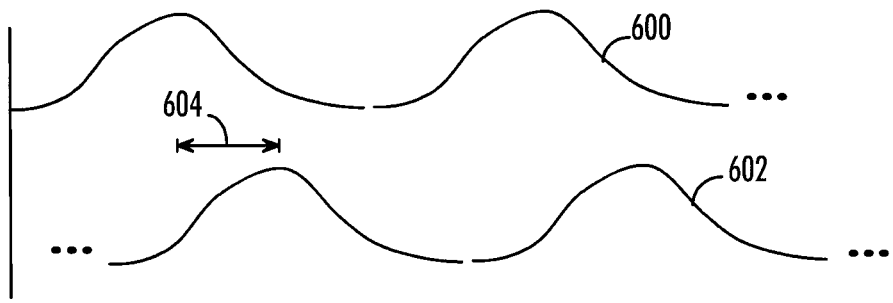
FIGS. 6A, 6B, 6C, and 6D illustrate detected exemplary heart pulse waveforms.

FIGS. 6A to 6D show detected pulse waveforms 600 and 602 by two detectors, such as detectors 104 and 106, respectively. In general, the detector detects the blood pulses and provides a waveform 600/602 of the detections of the blood pulses to the processor. In FIG. 6A, a blood pulse is detected by the detector 104 before the blood pulse is detected by the detector 106. The delay between the detections is marked with reference numeral 604. The detectors 104 and 106 provide the processor with the detected blood pulse waveforms 600 and 602. By obtaining information related to these, the processor may determine whether or not the order of the detections is as expected and if the detection is to be determined as true (valid, correct, successful) detection or false (erroneous) detection. That is, whether or not the at least one detector 104 and 106 has detected a blood pulse or is the detection due to a motion artifact, for example. The processor may further consider whether or not the time difference 604 between the detections is according to the known time difference. The consideration of the time difference 604 may also be taken into account when determining whether or not the detection is valid. In the case of FIG. 6A, the detection may be determined as correct.

Figure 6B:
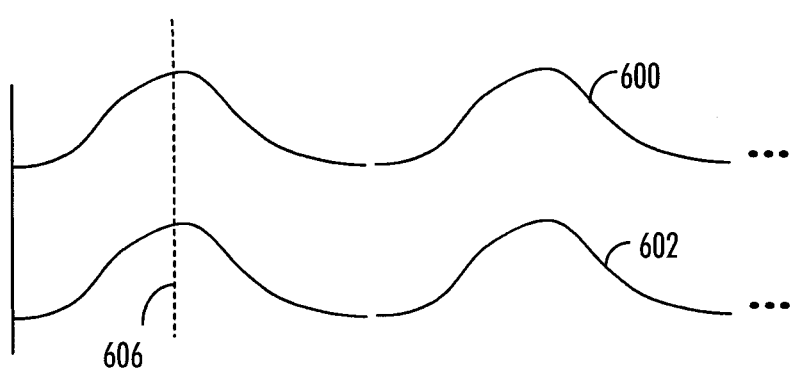

In FIG. 6B, the detections of the blood pulses by the two detectors have taken place at the same time. That is, the pulses coincide. This is shown in the blood pulse waveforms 600 and 602. Simultaneous detection is not possible because the detectors are placed in such a way on the person that the detections cannot take place simultaneously. For example, when the detectors are placed along a single artery and blood flows in the artery only in a single direction, it is not possible to detect the blood pulse simultaneously by both of the detectors. When the detectors are placed one in each arm, for example, the distances from the origin of the heart pulses are selected such that the detection cannot happen simultaneously. As the detections in FIG. 6B occur simultaneously, no requirement for the known order and no requirement for the known time difference are fulfilled. Therefore, the processor determines that the detection as shown in FIG. 6B is erroneous and is not taken into account when determining the heart pulse of the person.

Figure 6C:
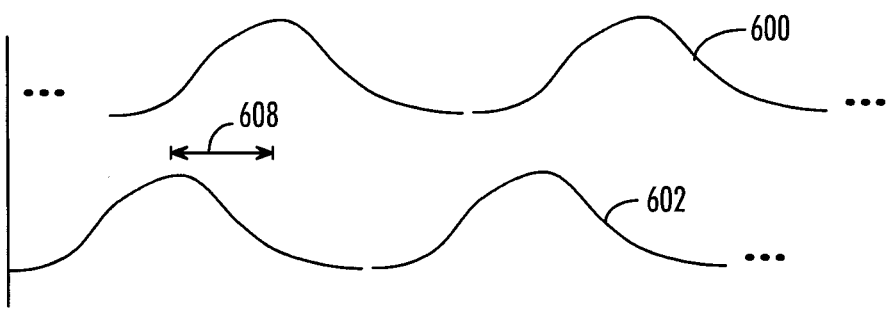

FIG. 6C is similar to FIG. 6A, but in FIG. 6C the detections take place in an opposite order, that is, the blood pulse waveform 602 indicates that the detection by the detector 106 is observed first and then, after a time duration 608, the blood pulse is detected by the detector 104. This is not possible when the detectors are placed so that the detector 104 is expected to detect the pulse waveform 600 first. As a consequence, the processor determines that the detection as shown in FIG. 6C is erroneous and is therefore not taken into account when determining the heart pulse of the person.

Figure 6D:
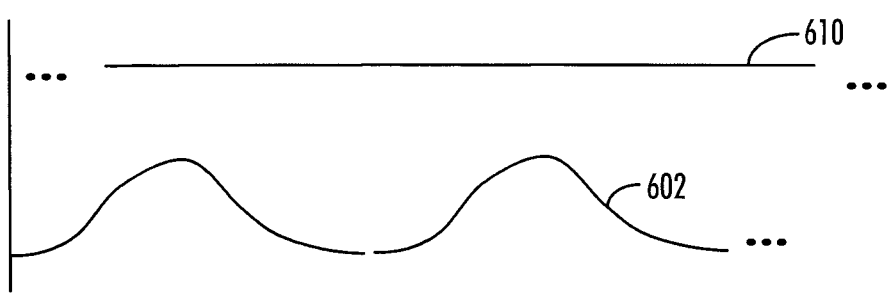

In FIG. 6D, the detector 104 has not been able to detect a blood pulse correctly and obtains only a flat pulse waveform 610. Therefore, the detector 104 may report nothing to the processor. However, the detector 106 has provided the processor with a blood pulse waveform 602. The processor obtaining only one pulse form may determine that the detection is correct and the missed detection of the detector 104 is not severe. However, the processor may also determine that because it did not receive detection information from each of the detectors 104 and 106, the detection is not reliable and, therefore, the detection is determined as false detection and not taken into account when determining the heart pulse.

According to an embodiment, in the case of multiple detectors, the processor needs to obtain a correct detection from at least a predetermined number of detectors. That is, not all of the detectors need to provide correct detection results, but it is enough if the predetermined number of the at least two detectors provide the processor with correct detections. A correct detection means that the detections by the predetermined number of detectors took place in the known order and were possibly also separated by the known time difference(s).

FIG. 5C shows a further embodiment of the apparatus for determining heart pulses of the person. In this embodiment, there is a further detector 512 which may detect the blood pulse optically. The further detector 512 may be placed optically on the skin of the person. The further detector 512 may be expected to detect the blood pulse substantially at the same time as one of the at least two detectors 104 and 106, known as a reference detector. This may be the case when the reference detector detects the pulse from an artery and the further detector 512 detects the pulse from the skin's microcirculation, for example. However, the further detector may detect the pulse from an artery other than the reference detector does, as long as the place along the other artery is equidistant from the heart as compared with the reference detector. The equidistant detectors allow the blood pulses to be detected substantially at the same time.

Figure 7:
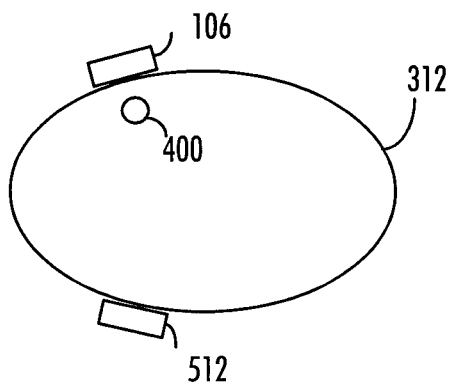
FIG. 7 illustrates an exemplary placement of detectors according to an embodiment.

According to an embodiment, the further detector 512 may be placed on a side of the wrist opposite to the reference detector. The further detector 512 may be placed at location 318 when the reference detector is at location 314, for example. This is shown in FIG. 7, where the one 106 of the at least two detectors being the reference detector is placed on the palm side of the wrist 312 and set to detect the blood pulse from an artery 400. The further detector 512 is then placed on the back side of the wrist 312 and set to detect the blood pulse from the microcirculation of the person.

When the further detector 512 is applied, the processor 102 may determine that a blood pulse has been detected when the detection of the blood pulse by the further detector 512 takes place substantially at the same time as the detection of the blood pulse by the reference detector 106. In this case, it can be said that the detection of the blood pulse is correct, valid, or successful. As a consequence, the use of a further detector 512 enables improved reliability of the pulse detection.

Figure 8A:
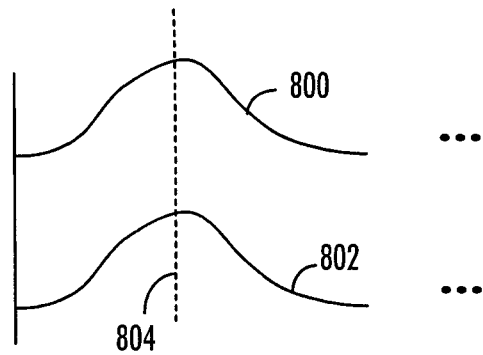
FIGS. 8A and 8B illustrate detected exemplary heart pulse waveforms.
Figure 8B:
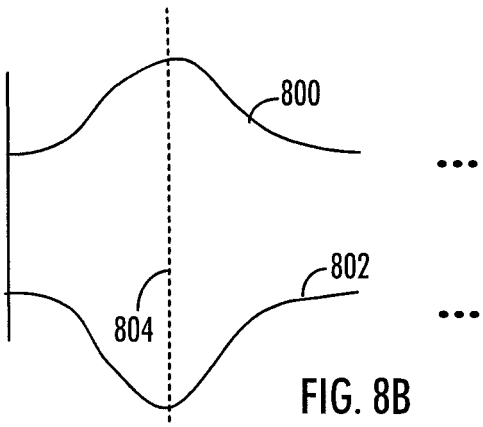

FIG. 8 shows blood pulse waveforms 800 and 802 resulting from blood pulse detections by one 106 of the at least two detectors and by the further detector 512, respectively. In FIG. 8A, according to the blood pulse waveform 800 obtained by the reference detector 106 the detection of the blood pulse takes place substantially at the same time as the detection of the blood pulse by the further detector 512. The simultaneous time instant is shown in FIGS. 8A and 8B by reference numeral 804. Therefore, the processor obtaining information on the detections may determine that the detection is correct and is taken into account when determining the heart pulses of the person.

The processor 102 may further take into account the phase of the pulse waveforms 800 and 802 obtained by the reference detector 106 and the further detector 512. In FIG. 8A, the pulse waveforms 800 and 802 are substantially at the same phase, or at least the difference in the phase is constant and the constant phase difference is possibly learnt beforehand. Therefore, even if the processor 102 is to take the phase of the pulse waveforms 800 and 802 into account, the processor 102 may determine that the detection in FIG. 8A is correct and it is taken into account when determining the heart pulses of the person.

In FIG. 8B, the blood pulse waveforms 800 and 802 show simultaneous detection of the blood pulse, but the phase of the pulse waveforms 800 and 802 are not substantially the same. This may be due to a motion artifact causing a false detection because the relative motion between the skin and the detector 106/512 causes variation in the detected optical radiation that is reflected from the tissue. Therefore, the variation may cause the detector to erroneously assume that a blood pulse is present. A detected motion artifact is typically seen as having a different, random phase as compared with the other detection. The different phases may be opposite to each other, as is the case in FIG. 8B. This is because the tissue on one side of the wrist becomes tighter as the detector on that side may press down the tissue underneath, whereas the detector on the other side of the wrist may disengage from the tissue underneath, especially in a case where the detector 106 and the further detector 512 are placed on the opposite sides of the wrist 312 and embodied along the same wrist band. Therefore, the processor may determine that the detection as shown in FIG. 8B is erroneous and the detection is not taken into account when determining the heart pulses of the person.

By applying the further detector 510, the reliability of the detection improves. For example, when the detection by the at least two detectors 104 and 106 is determined as correct (i.e., a correct known order and possibly also a correct known time difference between the detections), but the detection by the further detector 512 is determined as false due to non-simultaneousness and/or due to different phases of the heart pulse waveforms 800 and 802, the detection may finally be determined as false and not to be taken into account in the determination of the heart pulse of the person. The determination regarding the correctness of the detection by the further detector 512 need not be considered if the detection by the at least two detectors is already determined as erroneous. Thus, in an embodiment, the detection is determined as correct only when the detection of the at least two detectors 104 and 106 is valid (i.e., according to a known order and possibly also according to a known time difference) and the further detector 512 detects the blood pulse substantially at the same time as the reference detector, wherein the reference detector is one of the at least two detectors 104 and 106. A further requirement for the detection by the further detector 512 may be that the detected heart pulse is substantially at the same phase as the blood pulse detected by the reference detector.

In an embodiment of the invention, the optical measurement is based on pulse oximetry, wherein oxygen is bound to the blood hemoglobin. A blood oximetry measurement may be based on 660 nm (red) and/or 940 nm (infrared) optical radiations. The measurement may therefore apply two optical radiation sources having different wavelengths and pulsed at a high current (100 to 200 mA). The changing absorbance of each of the two wavelengths is measured, allowing determination of the absorbance due to the pulsing blood alone. Based upon a ratio of changing absorbance of the red and infrared light, a measure of oxygenation can be made. The oxygenation may denote the percentage of hemoglobin molecules bound with oxygen molecules. Therefore, according to an embodiment, the processor may determine the oxygen saturation level from the detected blood pulses by comparing the amount of the detected reflected optical radiation having different wavelengths. This is advantageous in that the user is informed of his or her oxygen saturation level during the exercise.

The heart pulse detection may be based on a correlation between two pulses wherein one of the pulses is time-shifted by the known delay. When the correlation is higher than a predetermined threshold, the detection of the heart pulse is determined as correct. Otherwise the detection is determined as false. In one embodiment, the blood flow in a vein is measured as well as the blood flow in an artery (possibly with different wavelengths). As a result, the processor may correlate the reflected optical radiation signal detected by the at least two detectors in order to verify the presence of a blood pulse. These signals have a good correlation in the case of a true pulse. Contrarily, noise signal detection happens randomly with a low correlation. Noise signal detection means detection due to a motion artifact, for example.

In one embodiment, the apparatus of FIGS. 1, 2 and 5 has a teaching mode during which the system is calibrated with the time delay and the order of the pulses detected by the detectors. The teaching mode may be run by the user. In this case, the user may be instructed not to generate unnecessary motion so that no erroneous detections are made. In another embodiment, the apparatus detects pulses from each detector and studies the time structure of the pulses. The assessment of whether the pulses are appropriate or not for calibration can be done retroactively. Accordingly, the processor may allow calibration of at least one of the following: the known order of the blood pulse detections with respect to the person, and the known time difference between the blood pulse detections with respect to the person. Further, the processor may be provided with information related to propagation characteristics of the blood circulation of the person. The processor may obtain this information itself by analyzing the detections, or the user may give such information to the apparatus. The propagation information may include the velocity of the blood pulses, for example.

According to an embodiment, the detectors 104, 106 and possibly also the further detector 512 may be embodied in a glove that the person wears on his or her hand during use. The glove may be manufactured out of neoprene, for example. Suitable places for placing the detectors and possibly also the at least one optical light source in the glove are along the fingers of the hand, the tips of the fingers, and the palm of the hand, for example. This embodiment allows for a possibility to easily add many detectors in one simple, yet robust, entity. This embodiment is also especially suitable for computer games where the heart rate of the player is of interest. In the context of computer games, the glove may be connected wirelessly or via a wire to a game console or a personal computer running the game.

According to yet another embodiment, the apparatus for determining the heart pulse comprises one or more acceleration sensors or motion sensors. The information provided by the sensors may be used in further eliminating erroneous pulse detection by knowing when a potential motion artifact has occurred.

Figure 9:
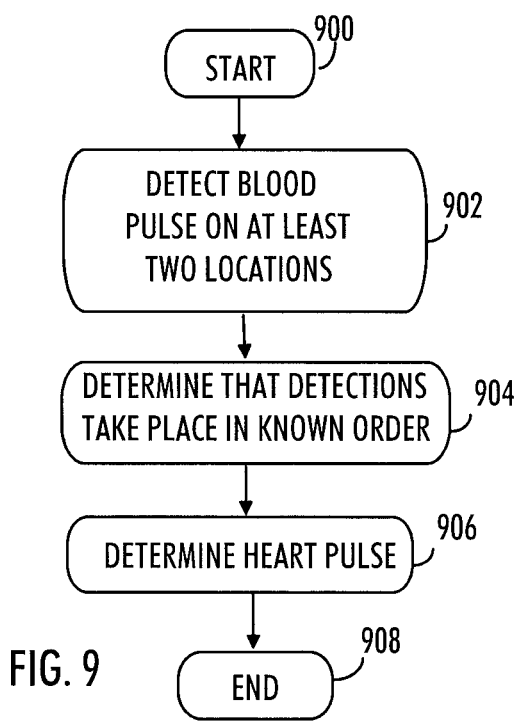
FIG. 9 presents a method for determining a person's heart pulse according to an embodiment.

A method for determining person's heart pulses is given in FIG. 9. The method begins in step 900. In step 902, detection of a blood pulse optically from the blood circulation of the person on at least two locations takes place. The locations are selected such that the detection of the blood pulse at these at least two locations is expected to take place in a known order. Step 904 of the method comprises determining that the blood pulse has been detected when the detections by the at least two detectors take place in the known order. In step 906, the heart pulse of the person is determined on the basis of the detected blood pulse. The method ends in step 908.

The techniques and methods described herein may be implemented by various means. For example, these techniques may be implemented by hardware (one or more devices), firmware (one or more devices), software (one or more modules), or combinations thereof. For a hardware implementation, the apparatuses of FIGS. 1, 2, and 5 may each be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Thus, according to an embodiment, the apparatus for performing the tasks of FIGS. 1 to 9 comprises at least two detection means for detecting a blood pulse optically from the blood circulation of the person. The detection means are to be placed optically on the skin of the person. The apparatus further comprises processing means for determining that the blood pulse has been detected when the detections by the at least two detectors take place in a known order, and for determining the heart pulse of the person on the basis of the detected blood pulse.

Embodiments of the invention may be implemented as computer programs in the apparatuses of FIGS. 1, 2, and 5 according to embodiments of the invention. The computer program implemented in any of the apparatuses of FIGS. 1, 2, and 5 may carry out, but is not limited to, the tasks related to FIGS. 1 to 9.

The computer program may be stored on a computer program distribution medium readable by a computer or a processor. The computer program medium may be, for example but not limited to, an electric, magnetic, optical, infrared or semiconductor system, device or transmission medium. The computer program medium may include at least one of the following media: a computer readable medium, a program storage medium, a record medium, a computer readable memory, a random access memory, an erasable programmable read-only memory, a computer readable software distribution package, a computer readable signal, a computer readable telecommunications signal, computer readable printed matter, and a computer readable compressed software package.

Even though the invention has been described above with reference to an example according to the accompanying drawings, it is clear that the invention is not restricted thereto but can be modified in several ways within the scope of the appended claims. Further, it is clear to a person skilled in the art that the described embodiments may, but are not required to, be combined with other embodiments in various ways.

What is claimed is:

1. An apparatus for determining a heart rate of a person, the apparatus comprising:
at least two detectors configured to detect a blood pulse optically from the blood circulation of the person and to be placed in optical communication with and substantially adjacent to the skin of the person, wherein the blood pulse is detected by the at least two detectors from a same body part; and
a processor configured to verify that the blood pulse has been detected based on whether a first detection of the blood pulse associated with one of the at least two detectors occurs before a second detection of the blood pulse associated with another of the least two detectors, the processor being configured to determine the heart rate of the person on the basis of the detected blood pulse, wherein the processor is further configured to verify that the blood pulse has been detected based on whether the detections by the at least two detectors are separated by a predetermined time difference.

2. The apparatus of claim 1, wherein the at least two detectors are further configured to detect a variation in optical radiation reflected from the human tissue in order to detect the blood pulse from the blood circulation optically, wherein the detection of the blood pulse comprises obtaining knowledge of at least one of the following: a time instant, form and phase of a blood pulse waveform.

3. The apparatus of claim 2, wherein the apparatus further comprises at least one optical radiation source configured to provide optical radiation such that the at least two detectors are able to detect the optical radiation reflected from the human tissue.

4. The apparatus of claim 2, further comprising a signal processing chain connected to the at least two detectors that enables the detection of the blood pulse optically when the reflected optical radiation to be detected originates only from ambient optical radiation.

5. The apparatus of claim 1, wherein the at least two detectors are further configured to detect the blood pulse from at least one of the following: the arterial blood flow, the venous blood flow, and the microcirculation, of the person.

6. The apparatus of claim 1, wherein the processor and the at least two detectors are comprised in a wrist device.

7. The apparatus of claim 6, wherein the apparatus further comprises at least one optical radiation guide embodied in at least one wrist band having an optical fiber cable that conveys the optical radiation to an area of the skin such that the at least two detectors are able to detect the reflected optical radiation.

8. The apparatus of claim 1, further comprising a gauge unit equipped with the at least two detectors, the at least one light source, and a transmitter configured to transmit detection results to a main unit equipped with the processor.

9. The apparatus of claim 1, further comprising a further detector configured to detect the blood pulse optically and to be placed in optical communication with and substantially adjacent to the skin of the person, wherein the processor is further configured to determine that the blood pulse has been detected when the detection of the blood pulse by the further detector takes place substantially at the same time as the detection of the blood pulse by a reference detector being one of the at least two detectors.

10. The apparatus of claim 9, wherein the further detector is configured to be placed in optical communication with and substantially adjacent to a side of the wrist opposite to the one of the at least two detectors.

11. The apparatus of claim 1, wherein the optical radiation is provided at two different wavelengths, the processor being further configured to determine an oxygen saturation level from the detected blood pulse by comparing the amount of the detected reflected optical radiation having different wavelengths.

12. The apparatus of claim 1, wherein the processor is further configured to correlate the reflected optical radiation signals detected by the at least two detectors in order to verify the presence of a blood pulse.

13. The apparatus of claim 1, wherein the processor is further configured to allow for calibration of at least one of the following: the known order of the blood pulse detections with respect to the person and the known time difference between the blood pulse detections with respect to the person.

14. The apparatus of claim 1, wherein the processor and the at least two detectors are comprised in a single-casing.

* * * * *